(12) United States Patent
Kang et al.

(10) Patent No.: US 11,875,893 B2
(45) Date of Patent: Jan. 16, 2024

(54) METHOD AND APPARATUS FOR OUTPUTTING INFORMATION RELATED TO A PATHOLOGICAL SLIDE IMAGE

(71) Applicant: LUNIT INC., Seoul (KR)

(72) Inventors: Jeong Seok Kang, Yongin-si (KR); Jae Hong Aum, Seoul (KR); Dong Geun Yoo, Seoul (KR); Tai Won Chung, Seoul (KR)

(73) Assignee: LUNIT INC., Seoul (KR)

( * ) Notice: Subject to any disclaimer, the term of this patent is extended or adjusted under 35 U.S.C. 154(b) by 0 days.

(21) Appl. No.: 18/102,465

(22) Filed: Jan. 27, 2023

(65) Prior Publication Data

US 2023/0178220 A1 Jun. 8, 2023

Related U.S. Application Data

(63) Continuation of application No. PCT/KR2022/011308, filed on Aug. 1, 2022.

(30) Foreign Application Priority Data

Aug. 10, 2021 (KR) .................. 10-2021-0105189
Jul. 28, 2022 (KR) .................. 10-2022-0093637

(51) Int. Cl.
*G16H 30/40* (2018.01)
*G16H 10/40* (2018.01)

(52) U.S. Cl.
CPC ............. *G16H 30/40* (2018.01); *G16H 10/40* (2018.01)

(58) Field of Classification Search
CPC .............................. G16H 30/40; G16H 10/40

USPC ........................................................... 705/2
See application file for complete search history.

(56) References Cited

U.S. PATENT DOCUMENTS

| | | | |
|---|---|---|---|
| 2011/0181622 A1* | 7/2011 | Bacus | G06T 3/00 345/634 |
| 2014/0030737 A1* | 1/2014 | Holmes | G01N 21/645 435/7.1 |
| 2020/0074146 A1* | 3/2020 | Prabhudesai | G06V 20/698 |
| 2020/0294231 A1* | 9/2020 | Tosun | G06V 10/7784 |
| 2020/0372635 A1* | 11/2020 | Veidman | G06V 20/69 |

(Continued)

FOREIGN PATENT DOCUMENTS

| | | |
|---|---|---|
| KR | 10-2010-0102560 A | 9/2010 |
| KR | 10-2015-0023760 A | 3/2015 |

(Continued)

OTHER PUBLICATIONS

International Search Report for PCT/KR2022/011308 dated, Oct. 28, 2022 (PCT/ISA/210).

*Primary Examiner* — Michael Tomaszewski
(74) *Attorney, Agent, or Firm* — Sughrue Mion, PLLC

(57) ABSTRACT

A computing apparatus includes: at least one memory; and at least one processor, wherein the processor generates quantitative information regarding at least one cell included in a region of interest of a pathological slide image by analyzing the pathological slide image, generates qualitative information regarding at least one tissue included in the pathological slide image by analyzing the pathological slide image, and controls a display apparatus to output at least one of the quantitative information and the qualitative information on the pathological slide image according to a manipulation of a user.

13 Claims, 16 Drawing Sheets

(56) References Cited

U.S. PATENT DOCUMENTS

| | | | |
|---|---|---|---|
| 2020/0394796 A1* | 12/2020 | Song | G06T 7/11 |
| 2022/0076411 A1* | 3/2022 | Georgescu | G06V 20/695 |
| 2022/0084660 A1* | 3/2022 | Georgescu | G16H 30/40 |
| 2022/0309653 A1* | 9/2022 | Hassanpour | G06V 10/82 |

FOREIGN PATENT DOCUMENTS

| | | | | |
|---|---|---|---|---|
| KR | 10-2015-0036757 A | 4/2015 | | |
| KR | 10-2016-0052442 A | 5/2016 | | |
| WO | WO-2019143633 A1 * | 7/2019 | | G06T 7/0012 |
| WO | WO-2020037255 A1 * | 2/2020 | | G06K 9/0014 |
| WO | WO-2020168284 A1 * | 8/2020 | | G02B 21/365 |

* cited by examiner

FIG. 13
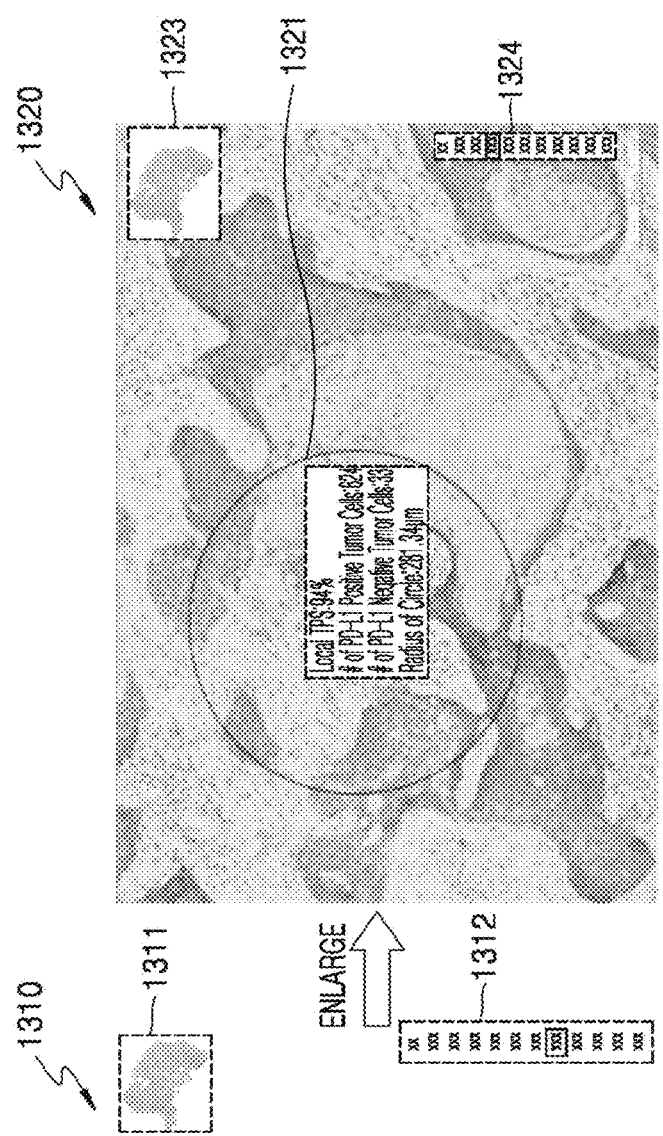

METHOD AND APPARATUS FOR OUTPUTTING INFORMATION RELATED TO A PATHOLOGICAL SLIDE IMAGE

CROSS REFERENCE TO RELATED APPLICATIONS

This application is a Bypass Continuation of PCT/KR2022/011308 filed Aug. 1, 2022, claiming priority based on Korean Patent Application No. 10-2021-0105189 filed on Aug. 10, 2021 and Korean Patent Application No. 10-2022-093637 filed Jul. 28, 2022.

TECHNICAL FIELD

The present disclosure relates to a method and apparatus for outputting information related to a pathological slide image.

BACKGROUND ART

The field of digital pathology refers to a field of acquiring histological information or predicting a prognosis of a subject by using a whole slide image generated by scanning a pathological slide image.

The pathological slide image may be acquired from a stained tissue sample of the subject. For example, a tissue sample may be stained by various staining methods, such as hematoxylin and eosin, trichrome, periodic acid schiff, autoradiography, enzyme histochemistry, immuno-fluorescence, and immunohistochemistry. The stained tissue sample may be used for histology and biopsy evaluations, and thus may operate as a basis for determining whether or not to move on to molecular profile analysis to understand a disease state.

In general, the pathological slide image is displayed together with a tissue segmentation result, a cell detection result, and the like. However, a user performs reading while enlarging or reducing the pathological slide image, and thus, information output together with the pathological slide image needs to be also changed in response to a manipulation of the user.

DETAILED DESCRIPTION OF THE INVENTION

Technical Problem

The present disclosure provides a method and apparatus for outputting information related to a pathological slide image. The present disclosure also provides a computer-readable recording medium recording thereon a program for executing the method on a computer. The objects to be achieved are not limited to the objects as described above, and other objects may be obtained.

Technical Solution to Problem

According to an aspect, a computing apparatus includes: at least one memory; and at least one processor, wherein the processor generates quantitative information regarding at least one cell included in a region of interest of a pathological slide image by analyzing the pathological slide image, generates qualitative information regarding at least one tissue included in the pathological slide image by analyzing the pathological slide image, and controls a display apparatus to output at least one of the quantitative information and the qualitative information on the pathological slide image according to a manipulation of a user.

According to another aspect, a method of outputting information regarding a pathological slide image includes: generating quantitative information regarding at least one cell included in a region of interest of a pathological slide image by analyzing the pathological slide image; generating qualitative information regarding at least one tissue included in the pathological slide image by analyzing the pathological slide image; and outputting at least one of the quantitative information and the qualitative information on the pathological slide image according to a manipulation of a user.

According to another aspect, a computer-readable recording medium includes a recording medium recording thereon a program for executing the above-described method on a computer.

BRIEF DESCRIPTION OF DRAWINGS

FIGS. 13 and 14 are views illustrating examples in which quantitative information and qualitative information are output, according to an embodiment.

BEST MODE

Figure 1:
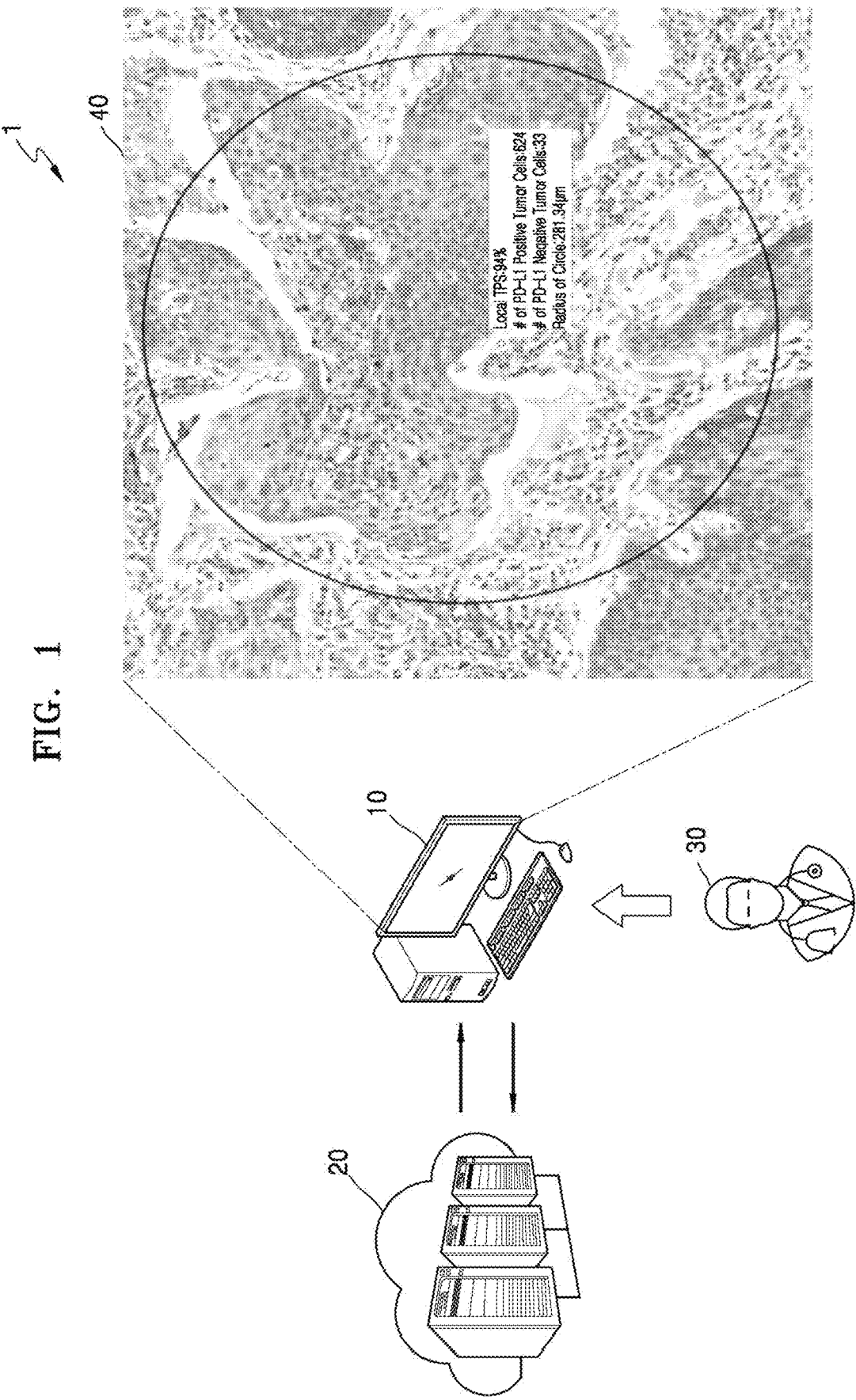
FIG. 1 is a view illustrating an example of a system for outputting information regarding a pathological slide image, according to an embodiment.

A computing apparatus according to an aspect includes: at least one memory; and at least one processor, wherein the processor generates quantitative information regarding at least one cell included in a region of interest of a pathological slide image by analyzes the pathological slide image, and generates qualitative information regarding at least one tissue included in the pathological slide image by analyzing the pathological slide image, and controls a display apparatus to output at least one of the quantitative information and the qualitative information on the pathological slide image according to a manipulation of a user.

Mode of Disclosure

Terms used in embodiments are selected as currently widely used general terms as possible, which may vary depending on intentions or precedents of one of ordinary skill in the art, emergence of new technologies, and the like. In addition, in certain cases, there are also terms arbitrarily selected by the applicant, and in this case, the meaning thereof will be defined in detail in the description. Therefore, the terms used herein should be defined based on the meanings of the terms and the details throughout the description, rather than the simple names of the terms.

Throughout the description, when a part includes a certain element, it means that other elements may be further included, rather than excluding the other elements, unless otherwise stated. In addition, the term, such as "~unit" or "~module" described herein, refers to a unit that processes at least one function or operation, which may be implemented as hardware or software, or a combination of hardware and software.

Also, although the terms, "first", "second", etc. may be used herein to describe various elements, these elements should not be limited by these terms. These terms may be only used to distinguish one element from another.

According to an embodiment, "a pathological slide image" may refer to an image obtained by photographing a pathological slide that is fixed and stained via a series of chemical treatment processes for tissue or the like removed from a human body. In addition, the pathological slide image may refer to a whole slide image (WSI) including a high-resolution image of a whole slide, and may also refer to a portion of the whole slide image, for example, one or more patches. For example, the pathological slide image may refer to a digital image captured or scanned via a scanning apparatus (e.g., a digital scanner or the like), and may include information regarding a particular protein, cell, tissue and/or structure within a human body. In addition, the pathological slide image may include one or more patches, and histological information may be applied (e.g., tagged) to the one or more patches via an annotation operation.

According to an embodiment, "medical information" may refer to any medically meaningful information that may be extracted from a medical image, and may include, for example, an area, location, and size of a tumor cell within a medical image, diagnostic information regarding cancer, information associated with a subject's possibility of developing cancer, and/or a medical conclusion associated with cancer treatment, but is not limited thereto. In addition, the medical information may include not only a quantified numerical value that may be obtained from a medical image, but also information obtained by visualizing the numerical value, predictive information according to the numerical value, image information, statistical information, and the like. The medical information generated as described above may be provided to a user terminal or output or transmitted to a display apparatus to be displayed.

Hereinafter, embodiments will be described in detail with reference to the accompanying drawings. However, the embodiments may be implemented in several different forms and are not limited to examples described herein.

FIG. 1 is a view illustrating an example of a system for outputting information regarding a pathological slide image, according to an embodiment.

Referring to FIG. 1, a system 1 includes a user terminal 10 and a server 20. For example, the user terminal 10 and the server 20 may be connected to each other by a wired or wireless communication method to transmit and/or receive data (e.g., image data or the like) to and/or from each other.

For convenience of description, although FIG. 1 illustrates that the system 1 includes the user terminal 10 and the server 20, the present disclosure is not limited thereto. For example, other external devices (not shown) may be included in the system 1, and operations of the user terminal 10 and the server 20 to be described below may be implemented by a single device (e.g., the user terminal 10 or the server 20) or more devices.

The user terminal 10 may be a computing apparatus that is provided with a display apparatus and a device (e.g., a keyboard, a mouse, or the like) for receiving a user input, and includes a memory and a processor. For example, the user terminal 10 may correspond to a notebook PC, a desktop PC, a laptop, a tablet computer, a smartphone, or the like, but is not limited thereto.

The server 20 may be an apparatus that communicates with an external device (not shown) including the user terminal 10. As an example, the server 20 may be an apparatus that stores various types of data including a pathological slide image, a bitmap image corresponding to the pathological slide image, and information (e.g., including quantitative information, qualitative information, and the like) generated by analysis of the pathological slide image. Alternatively, the server 20 may be a computing apparatus including a memory and a processor, and having an operation capability. When the server 20 is a computing apparatus, the server 20 may perform at least some of operations of the user terminal 10 to be described below with reference to FIGS. 1 to 16. For example, the server 20 may also be a cloud server, but is not limited thereto.

The user terminal 10 outputs an image 40 expressing at least one of quantitative information and qualitative information generated via analysis of a pathological slide image and/or a pathological slide.

Here, the quantitative information includes numerical information in various aspects of at least one cell or tissue included in a region of interest set on the pathological slide image. For example, the quantitative information may include the number of total cells (or particular types of cells) included in the region of interest, the density of total cells, the density of particular types of cells, a ratio between different cell types, and a proportion of particular types of cells to the total cells, an area of a whole tissue (or a particular type of tissue), a ratio between different tissue types, a proportion of a particular type of tissue to a whole tissue area, and the like. The quantitative information may include information in a text form or a graph form.

Meanwhile, the qualitative information includes information regarding a state of at least one tissue or cell included in the pathological slide image.

As an example, the qualitative information may include a feature of at least one tissue included in the pathological slide image. The qualitative information may include information representing a feature of a tissue in a corresponding color. For example, the feature of the tissue may indicate whether a ratio of PD-L1 positive cancer cells to PD-L1 negative cancer cells within a certain size circle region centered on each pixel is greater than or equal to a certain threshold value. For example, the feature of the tissue may indicate information regarding an immune phenotype (IP) corresponding to a partial region of the pathological slide image. For example, the IP may be expressed as at least one of immune inflamed, immune excluded, and immune desert according to what range a value calculated on the basis of at least one of the density of immune cells within a cancer area and/or the density of immune cells within a cancer stroma falls within.

As another example, the qualitative information may include a type of at least one tissue included in the pathological slide image. The qualitative information may include information representing the type of tissue in a corresponding color. For example, the type of tissue may include one of cancer, cancer stroma, necrosis, and background.

As another example, the qualitative information may include a type or feature of at least one cell included in the pathological slide image. The qualitative information may include information representing the type of cell in a corresponding color. For example, the type of cell may represent at least one of an immune cell, such as a tumor cell, a lymphocyte, or a macrophage, or a stromal cell, such as a fibroblast or adipocyte constituting a stroma around a tumor.

Also, the qualitative information may include information representing a feature of a cell in a corresponding color. For example, the feature of the cell may include information regarding whether or not a cell expresses a particular protein. For example, the qualitative information may include information indicating whether a corresponding cell is a programmed death-ligand 1 (PD-L1) positive tumor cell, PD-L1 negative tumor cell, PD-L1 positive lymphocyte, or a PD-L1 positive macrophage.

The pathological slide image may refer to an image obtained by photographing a pathological slide that is fixed and stained through a series of chemical treatment processes to observe, via a microscope, a tissue or the like removed from a human body. As an example, the pathological slide image may refer to a whole slide image including a high-resolution image of a whole slide. As another example, the pathological slide image may refer to a portion of the whole high-resolution slide image.

Meanwhile, the pathological slide image may refer to a patch region segmented into patch units from the whole slide image. For example, a patch may have a certain area size. Alternatively, the patch may refer to a region including each of objects included in a whole slide.

In addition, the pathological slide image may refer to a digital image captured by using a microscope, and may include information regarding cells, tissues, and/or structures in the human body.

The user terminal 10 generates quantitative information regarding at least one cell included in a region of interest of the pathological slide image and qualitative information regarding at least one tissue included in the pathological slide image by analyzing the pathological slide image. Here, the user terminal 10 may generate quantitative information and qualitative information by analyzing the pathological slide image, or may receive, from the server 20, quantitative information and qualitative information generated by analyzing the pathological slide image by the server 20.

In general, information output on the pathological slide image includes a tissue segmentation result, a cell detection result, and the like. The above results may need to undergo certain processing and then be output together with the pathological slide image to be effectively transferred to a user 30. For example, information output on a display apparatus may be adaptively changed when a user manipulates a pathological slide image (e.g., changes an output location, enlarges/reduces an image, and the like).

The user terminal 10 according to an embodiment outputs quantitative information or qualitative information in correspondence to the region of interest set according to a manipulation of the user 30 or at least a portion of the pathological slide image output on the display apparatus. Accordingly, the user 30 may be given effective help to read an image output on the display apparatus and diagnose a subject.

Meanwhile, for convenience of description, as described herein, the user terminal 10 generates quantitative information and qualitative information by analyzing a pathological slide image, and outputs at least one of the quantitative information and the qualitative information according to a manipulation of a user, but is not limited thereto. For example, at least some of operations performed by the user terminal 10 may also be performed by the server 20.

In other words, at least some of operations of the user terminal 10 described with reference to FIGS. 1 to 15 may be performed by the server 20. As an example, the server 20 may generate various types of information (e.g., quantitative information and qualitative information) related to tissues and cells by analyzing the pathological slide image. Also, the server 20 may transmit the generated information to the user terminal 10. As another example, the server 20 may generate various types of information related to tissues and cells, and may transmit, to the user terminal 10, information to be output to the display apparatus according to a manipulation of the user, among the generated information. However, the operation of the server 20 is not limited to that described above.

Figure 2:
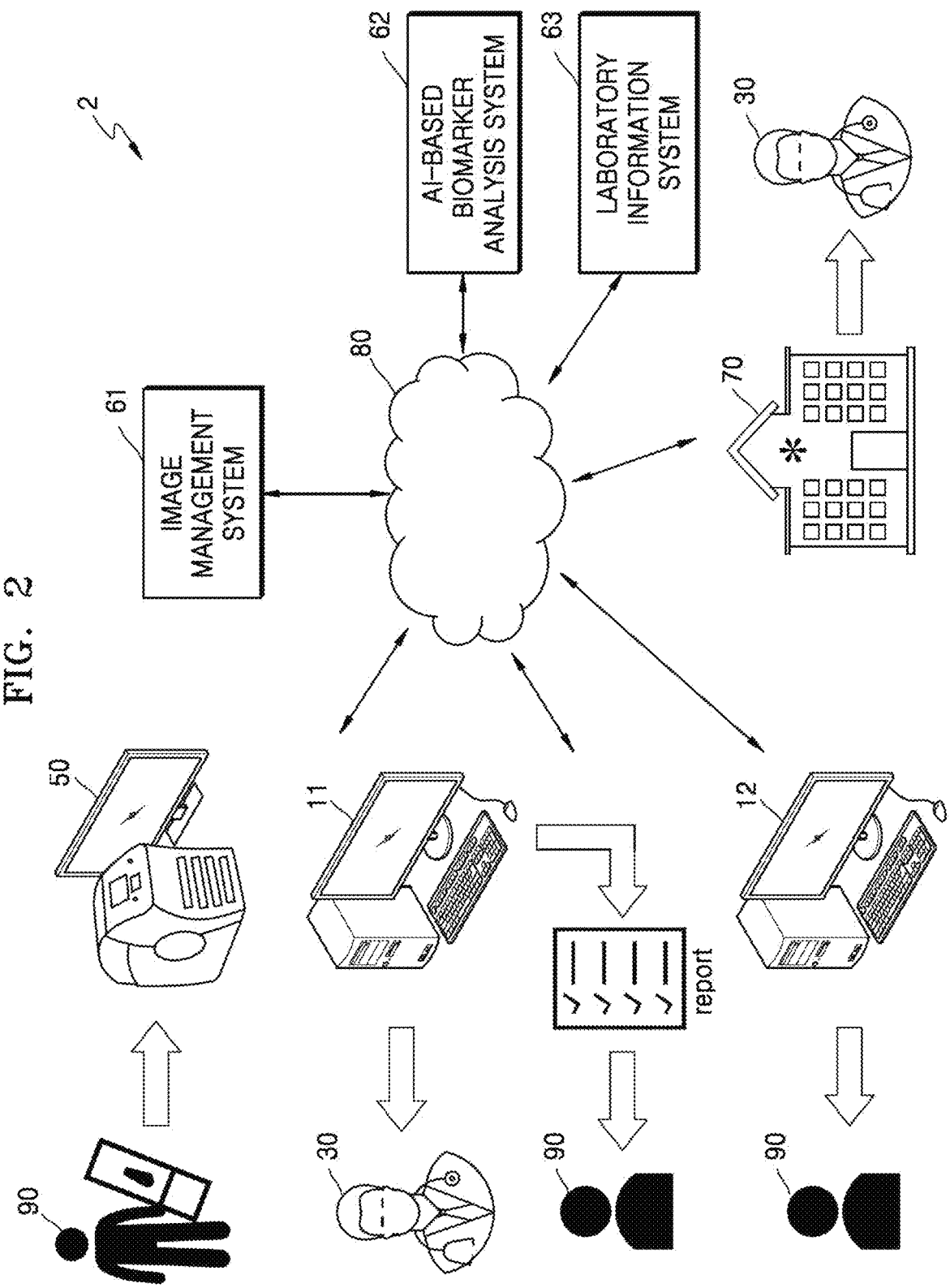
FIG. 2 is a block diagram of a system and a network for providing, processing, and reviewing slide images of tissue specimens by using machine learning, according to an embodiment.

FIG. 2 is a block diagram of a system and a network for providing, processing, and reviewing slide images of tissue specimens by using machine learning, according to an embodiment.

Referring to FIG. 2, a system 2 includes user terminals 11 and 12, a scanner 50, an image management system 61, an AI-based biomarker analysis system 62, a laboratory information system 63, and a server 70. In addition, the components (11, 12, 50, 61, 62, 63, and 70) included in the system 2 may be connected to one another via a network 80. For example, the network 80 may be a network via which the components (11, 12, 50, 61, 62, 63, and 70) may be connected to one another in a wired or wireless communication method. For example, the system 2 shown in FIG. 2 may include a network that may be connected to servers in hospitals, research rooms, laboratories, and the like, and/or user terminals of doctors or researchers.

According to various embodiments of the present disclosure, methods to be described below with reference to FIGS. 3A to 15 may be performed by the user terminals 11 and 12, the image management system 61, the AI-based biomarker analysis system 62, the laboratory information system 63, and/or the server 70.

The scanner 50 may acquire a digitized image from a tissue sample slide generated by using a tissue sample of a subject 90. For example, the scanner 50, the user terminals 11 and 12, the image management system 61, the AI-based biomarker analysis system 62, the laboratory information system 63, and/or the server 70 may be connected to the network 80, such as the Internet, via one or more computers, servers, and/or mobile devices, respectively, or may communicate with the user 30 and/or the subject 90 via one or more computers, and/or mobile devices.

The user terminals 11 and 12, the image management system 61, the AI-based biomarker analysis system 62, the laboratory information system 63, and/or the server 70 may generate or otherwise acquire, from another apparatus, one or more tissue samples of the subject 90, a tissue sample slide, digitized images of the tissue sample slide, or any combination thereof. In addition, the user terminals 11 and 12, the image management system 61, the AI-based biomarker analysis system 62, and the laboratory information system 63 may acquire any combination of subject-specific information, such as age, medical history, cancer treatment history, family history, and past biopsy records of the subject 90, or disease information of the subject 90.

The scanner 50, the user terminals 11 and 12, the image management system 61, the laboratory information system 63, and/or the server 70 may transmit digitized slide images and/or subject-specific information to the AI-based biomarker analysis system 62 via the network 80. The AI-based biomarker analysis system 62 may include one or more storage devices (not shown) for storing images and data received from at least one of the scanner 50, the user terminals 11 and 12, the image management system 61, the laboratory information system 63, and/or the server 70. In addition, the AI-based biomarker analysis system 62 may include an AI model repository that stores an AI model trained to process the received images and data. For example, the AI-based biomarker analysis system 62 may include an AI model that is learned and trained to predict, from a slide image of the subject 90, at least one of information regarding at least one cell, information regarding at least one region, information related to a biomarker, medical diagnostic information, and/or medical treatment information.

The scanner 50, the user terminals 11 and 12, the AI-based biomarker analysis system 62, the laboratory information system 63, and/or the server 70 may transmit a digitized slide image, subject-specific information, and/or a result of analyzing the digitized slide image to the image management system 61 via the network 80. The image management system 61 may include a repository for storing a received image and a repository for storing an analysis result.

In addition, according to various embodiments of the present disclosure, an AI model, which is learned and trained to predict, from a slide image of the subject 90, at least one of information regarding at least one cell, information regarding at least one region, information related to a biomarker, medical diagnostic information, and/or medical treatment information, may be stored in the user terminals 11 and 12 and/or the image management system 61 and operate.

According to various embodiments of the present disclosure, a slide image processing method, a subject information processing method, a subject group selection method, a clinical trial design method, a biomarker selection method, and/or a method of setting a reference value for a particular biomarker may be performed not only by the AI-based biomarker analysis system 62, but also by the user terminals 11 and 12, the image management system 61, the laboratory information system 63, and/or the server 70.

Figure 3A:
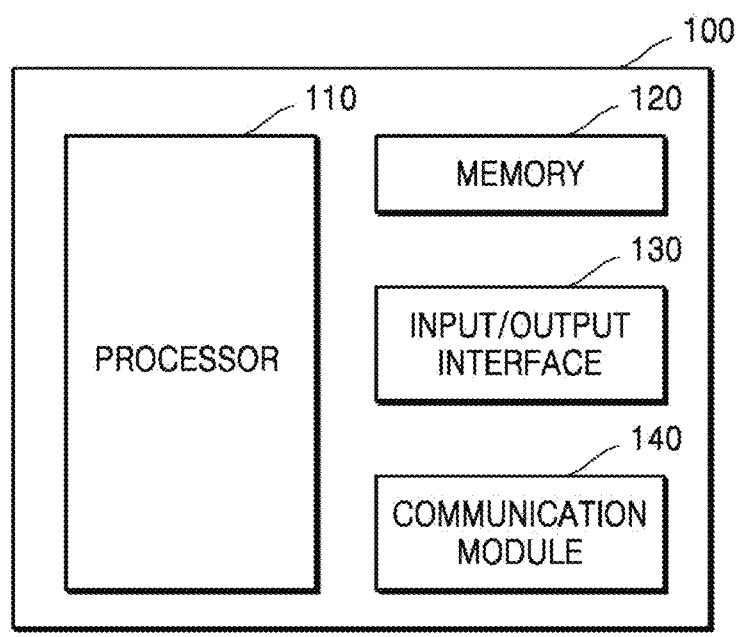
FIG. 3A is a block diagram illustrating an example of a user terminal according to an embodiment.

FIG. 3A is a block diagram illustrating an example of a user terminal according to an embodiment.

Referring to FIG. 3A, a user terminal 100 includes a processor 110, a memory 120, an input/output interface 130, and a communication module 140. For convenience of description, FIG. 3A illustrates only components related to the present disclosure. Accordingly, the user terminal 100 may further include other general-purpose components, in addition to the components shown in FIG. 3A. In addition, it is obvious to one of ordinary skill in the art related to the present disclosure that the processor 110, the memory 120, the input/output interface 130, and the communication module 140 shown in FIG. 3A may also be implemented as independent devices.

The processor 110 may process commands of a computer program by performing basic arithmetic, logic, and input/output operations. Here, the commands may be provided from the memory 120 or an external apparatus (e.g., the server 20 or the like). In addition, the processor 110 may control overall operations of other components included in the user terminal 100.

The processor 110 generates quantitative information regarding at least one cell included in a region of interest of a pathological slide image by analyzing the pathological slide image. For example, the processor 110 may analyze the pathological slide image by using a predetermined image processing technique, or may analyze the pathological slide image by using a machine learning model.

As an example, the processor 110 may generate a data structure by using coordinate information corresponding to each of cells included in the pathological slide image, and may identify, from the data structure, coordinate information corresponding to at least one cell included in the region of interest. Here, the data structure may be a tree efficient for searching for cells within the pathological slide image, and may be implemented as, for example, a K-D tree, a ball tree, or the like, but is not limited thereto. In addition, the processor 110 may generate quantitative information regarding cells on the basis of the number corresponding to the coordinate information. An example in which the processor 110 generates quantitative information by using a data structure will be described below with reference to FIG. 5.

As another example, the processor 110 may define a kernel on the basis of the region of interest, and may generate quantitative information via the pathological slide image and a used convolution operation. Here, at least one kernel may be defined according to a type of quantitative information. An example in which the processor 110 generates quantitative information via a convolution operation will be described below with reference to FIGS. 6 to 8.

The processor 110 generates qualitative information regarding at least one cell or tissue included in the pathological slide image by analyzing the pathological slide image. For example, the processor 110 may identify, on the basis of an analysis result of at least one cell or tissue, a label corresponding to the corresponding cell or tissue. Also, the processor 110 may convert a bitmap image corresponding to the pathological slide image on the basis of the label.

For example, the processor 110 may segment the bitmap image into a plurality of tiles on the basis of a resource of an apparatus (e.g., the user terminal 100) for converting a bitmap image, and may convert each of the tiles on the basis of the identified label. In addition, the processor 110 may complete the conversion of the bitmap image by combining the converted tiles. An example in which the processor 110 generates qualitative information will be described below with reference to FIGS. 9 and 10.

The processor 110 outputs at least one of quantitative information and qualitative information on the pathological slide image according to a manipulation of a user. For example, the processor 110 may change and output at least one of the quantitative information and the qualitative information on the basis of an output portion or an output magnification of the pathological slide image changed according to a manipulation of the user. Also, the processor 110 may change and output at least one of the quantitative information and the qualitative information by comparing the output magnification of the pathological slide image changed according to the user manipulation with a threshold magnification. An example in which the processor 110 controls an output of a display apparatus on the basis of a user's manipulation will be described below with reference to FIGS. 13 and 14.

The processor 110 may be implemented as an array of a plurality of logic gates, or may be implemented as a combination of a general-purpose microprocessor and a memory that stores a program executable by the microprocessor. For example, the processor 110 may include a general-purpose processor, a central processing unit (CPU), a microprocessor, a digital signal processor (DSP), a controller, a microcontroller, a state machine, or the like. In some environments, the processor 110 may include an application-specific integrated circuit (ASIC), a programmable logic device (PLD), a field programmable gate array (FPGA), or the like. For example, processor 110 may refer to a combination of processing devices, such as a combination of a digital signal processor (DSP) and a microprocessor, a combination of a plurality of microprocessors, a combination of one or more microprocessors combined with a digital signal processor (DSP) core, or a combination of any other such configurations.

The memory 120 may include any non-transitory computer-readable recording medium. As an example, the memory 120 may include a non-volatile (permanent) mass storage device, such as random access memory (RAM), read only memory (ROM), a disk drive, a solid state drive (SSD), or flash memory. As another example, the non-volatile mass storage device, such as ROM, an SSD, flash memory, or a disk drive, may be a separate permanent storage device distinguished from a memory. Also, the memory 210 may store an operating system (OS) and at least one program code (e.g., a code for the processor 110 to perform an operation to be described below with reference to FIGS. 4 to 15).

Software components described above may be loaded from a computer-readable recording medium separate from the memory 120. Such a separate computer-readable recording medium may be a recording medium that may be directly connected to the user terminal 100, and may include, for example, a computer-readable recording medium, such as a floppy drive, a disk, a tape, a DVD/CD-ROM drive, or a memory card. Alternatively, the software components may also be loaded into the memory 120 via the communication module 140 rather than a computer-readable recording medium. For example, at least one program may be loaded into the memory 120 on the basis of a computer program (e.g., a computer program for the processor 110 to perform an operation to be described below with reference to FIGS. 4 to 15, or the like) installed by files provided via the communication module 140 by developers or a file distribution system that distributes installation files of applications.

The input/output interface 130 may be a means for an interface with a device (e.g., a keyboard, a mouse, or the like) for an input or an output, which may be connected to the user terminal 100 or included in the user terminal 100. Although FIG. 3A illustrates that the input/output interface 130 is an element configured separately from the processor 110, the input/output interface 130 is not limited thereto, and may also be configured to be included in the processor 110.

The communication module 140 may provide a configuration or function for the server 20 and the user terminal 100 to communicate with each other via a network. In addition, the communication module 140 may provide a configuration or function for the user terminal 100 to communicate with another external device. For example, a control signal, a command, data, and the like, which are provided under control of the processor 110, may be transmitted to the server 20 and/or an external device through the communication module 140 and the network.

Meanwhile, although not shown in FIG. 3A, the user terminal 100 may further include a display apparatus. Alternatively, the user terminal 100 may be connected to an independent display apparatus via a wired or wireless communication method to transmit and/or receive data to and/or from each other. For example, a pathological slide image, quantitative information, qualitative information, and the like may be provided to the user 30 via the display apparatus.

Figure 3B:
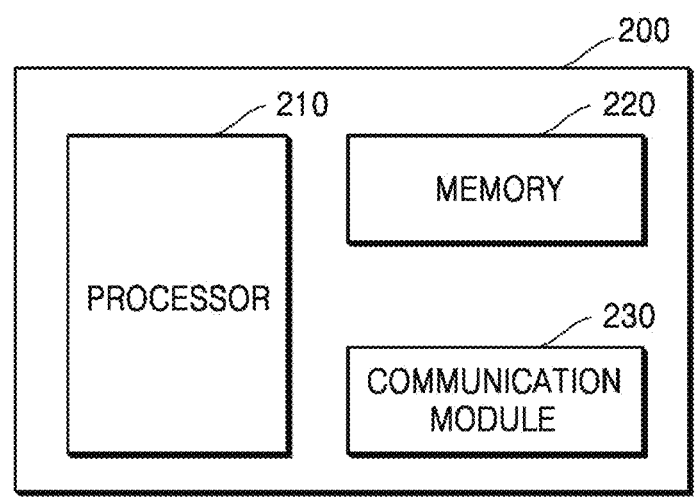
FIG. 3B is a block diagram illustrating an example of a server according to an embodiment.

FIG. 3B is a block diagram illustrating an example of a server according to an embodiment.

Referring to FIG. 3B, a server 200 includes a processor 210, a memory 220, and a communication module 230. For convenience of description, FIG. 3B illustrates only components related to the present disclosure. Accordingly, the server 200 may further include other general-purpose components, in addition to the components shown in FIG. 3B. In addition, it is obvious to one of ordinary skill in the art related to the present disclosure that the processor 210, the memory 220, and the communication module 230 shown in FIG. 3B may also be implemented as independent apparatuses.

The processor 210 may acquire a pathological slide image from at least one of the memory 220, an external memory (not shown), the user terminal 100, or an external apparatus. The processor 210 analyzes the pathological slide image to generate quantitative information regarding at least one cell included in a region of interest, generate qualitative information regarding at least one tissue included in the pathological slide image, or output at least one of the quantitative information and the qualitative information on the pathological slide image according to a user manipulation. In other words, at least one of the operations of the processor 110 described above with reference to FIG. 3A may be performed by the processor 210. In this case, the user terminal 100 may output, via a display apparatus, information transmitted from the server 200.

Meanwhile, the implementation example of the processor 210 is the same as the implementation example of the processor 110 described above with reference to FIG. 3A, and thus, a detailed description thereof will be omitted herein.

The memory 220 may store various types of data, such as the pathological slide image and data generated according to an operation of the processor 210. Also, the memory 220 may store an operating system (OS) and at least one program (e.g., a program required for the processor 210 to operate, or the like).

Meanwhile, the implementation example of the memory 220 is the same as the implementation example of the memory 120 described above with reference to FIG. 3A, and thus, a detailed description thereof will be omitted herein.

The communication module 230 may provide a configuration or function for the server 200 and the user terminal 100 to communicate with each other via a network. In addition, the communication module 230 may provide a configuration or function for the server 200 to communicate with another external apparatus. For example, a control signal, a command, data, and the like provided under control of the processor 210 may be transmitted to the user terminal 100 and/or an external device through the communication module 230 and the network.

Figure 4:
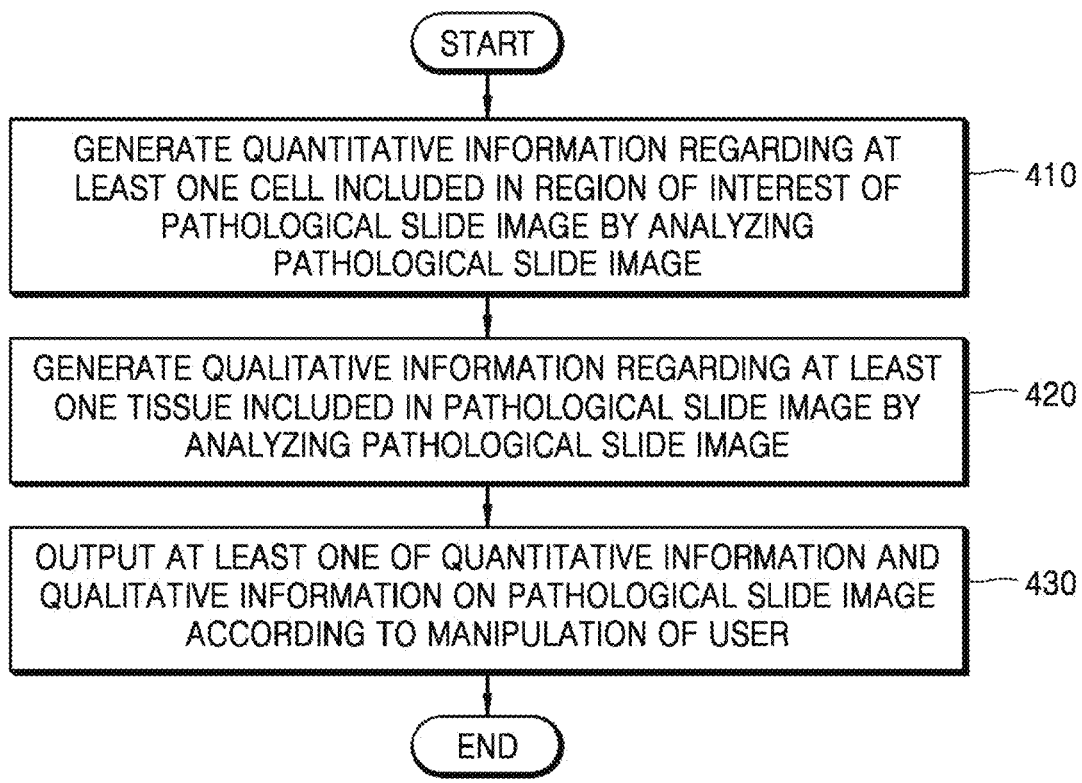
FIG. 4 is a flowchart illustrating an example in which a processor outputs information regarding a pathological slide image, according to an embodiment.

FIG. 4 is a flowchart illustrating an example in which a processor outputs information regarding a pathological slide image, according to an embodiment.

Referring to FIG. 4, a method of outputting information regarding a pathological slide image includes operations that are time-series processed by the user terminals 10 and 100 or the processor 110 illustrated in FIGS. 1 to 3B. Therefore, even when the above description of the user terminals 10 and 100 or the processor 110 shown in FIGS. 1 to 3B is omitted hereinafter, the above description may also be applied to the method of outputting information regarding a pathological slide image, illustrated in FIG. 4.

In addition, as described above with reference to FIGS. 1 to 3B, at least one of operations of the flowchart illustrated in FIG. 4 may be processed by the servers 20 and 200 or the processor 210.

In operation 410, the processor 110 generates quantitative information regarding at least one cell included in a region of interest of a pathological slide image by analyzing the pathological slide image.

As an example, the processor 110 may detect regions corresponding to tissues from the pathological slide image and separate layers representing the tissues by analyzing the pathological slide image by using a predetermined image processing technique. As another example, the processor 110 may perform detection of regions corresponding to tissues from the pathological slide image and separation of layers representing the tissues, by using a machine learning model. In this case, the machine learning model may be trained to use training data including a plurality of reference pathological slide images and a plurality of pieces of reference label information to detect regions corresponding to tissues within the reference pathological slide images and to separate layers representing the tissues. Accordingly, the processor 110 may acquire various types of information from the pathological slide image.

As an example, the processor 110 may acquire information regarding a region. The region may be one of a cancer area, a cancer stroma area, a necrosis area, and a background area. Here, the background area may include an area representing biological noise and/or an area representing technical noise. For example, the area representing the biological noise may include a normal area, and the area representing the technical noise may include a degraded area.

As another example, the processor 110 may acquire information regarding a cell. The cell may be one of a tumor cell, a lymphocyte cell, and other cells. For example, the processor 110 may acquire information regarding a cell (e.g., a PD-L1 positive cell) in which a particular protein is expressed, a cell (e.g., a PD-L1 negative cell) in which a particular protein is not expressed, an intratumoral tumor-infiltrating lymphocytes cell, or a stromal tumor-infiltrating lymphocytes cell.

As another example, the processor 110 may acquire other information regarding a cell, a region, or a tissue. For example, the processor 110 may identify a nuclei size, a cell density, the number of cells, a cell cluster, cell heterogeneity, spatial distances between the cells, and interaction between cells.

As another example, the processor 110 may acquire information 424 regarding a tumor microenvironment. Here, the tumor microenvironment refers to information regarding an environment surrounding a tumor, and includes, for example, information, such as presence or absence, location, type, quantity, and area of blood vessels, immune cells, fibroblasts, signaling molecules, and extracellular matrix (ECM) around the tumor.

The processor 110 generates the quantitative information regarding at least one cell included in the region of interest on the basis of the result of analyzing the pathological slide image.

Here, the region of interest may be a region requiring observation of the user 30 within the pathological slide image, a partial region selected within the pathological slide image, or a whole cell region within the pathological slide image. For example, the region of interest may be a region that needs to be significantly observed when pathologically reading a disease, but is not limited thereto. For example, when a diagnosis of lung cancer is required, a region in which lung cancer cells are present in a pathological slide image may be a region of interest, and when mitosis is evaluated in breast cancer, a region in which mitosis is expected to be high in a pathological slide image may be a region of interest. For example, the quantitative information may include at least one of a tumor proportion score (TPS), a combined positive score (CPS), and an intratumoral tumor-infiltrating lymphocytes density within the region of interest.

For example, the region of interest may be set according to a manipulation of the user 30. Also, any region of interest may be set on a pathological slide image output to a display apparatus, and then may be adjusted by the user 30. Meanwhile, the region of interest may be displayed in a circle, a rectangle, or the like on the pathological slide image, but is not limited thereto.

As an example, the processor 110 may generate quantitative information regarding the region of interest by using a data structure constructed on the basis of coordinate information of cells. As another example, the processor 110 may generate the quantitative information via a convolution operation. Hereinafter, examples in which the processor 110 generates quantitative information will be described with reference to FIGS. 5 to 8.

Figure 5:
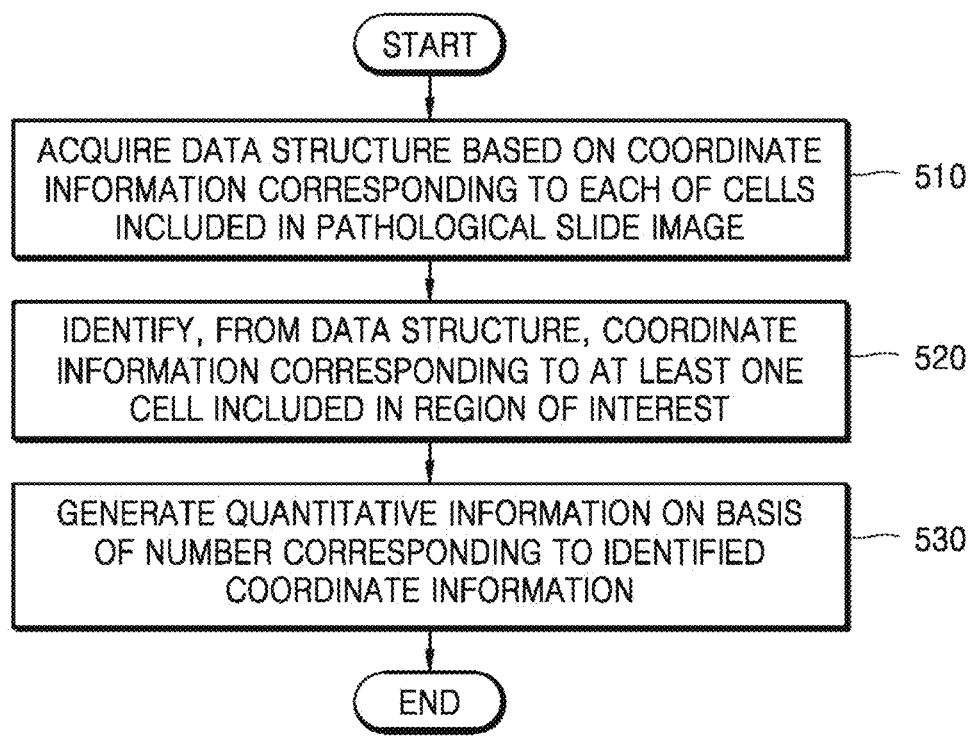
FIG. 5 is a flowchart illustrating an example in which a processor generates quantitative information, according to an embodiment.

FIG. 5 is a flowchart illustrating an example in which a processor generates quantitative information, according to an embodiment.

A pathological slide image may include coordinate values respectively corresponding to hundreds of thousands of cells. The processor 110 may generate quantitative information regarding how many particular types of cells are included in a region of interest, so that the user 30 effectively reads the pathological slide image.

In operation 510, the processor 110 acquires a data structure based on coordinate information corresponding to each of cells included in a pathological slide image. For example, the processor 110 may fetch a previously generated and stored data structure from a memory by using coordinate information, or may directly generate a data structure by using coordinate information.

As an example, the processor 110 may load a data structure generated on the basis of a coordinate value corresponding to each of total cells expressed in the pathological slide image. A size or location of a region of interest may be changed in real time according to a manipulation of the user 30. The processor 110 needs to efficiently search for a cell at a particular location from hundreds of thousands of cells to provide quantitative information in real time according to a change in the size or location of the region of interest. Accordingly, the data structure acquired in operation 510 may be a structure having high data retrieval efficiency rather than a structure having high data insertion or removal efficiency.

For example, the data structure may be a tree efficient for searching for cells within the pathological slide image, and may be implemented as, for example, a K-D tree, a ball tree, or the like, but is not limited thereto. The data structure described above may also be used when visualizing locations of cells within an image area output to a display apparatus.

As another example, the processor 110 identifies a coordinate value corresponding to each of total cells expressed in the pathological slide image. Also, the processor 110 generates a data structure by using the identified coordinate values.

A size or location of a region of interest may be changed in real time according to a manipulation of the user 30. The processor 110 needs to efficiently search for a cell at a particular location from hundreds of thousands of cells to provide quantitative information in real time according to a change in the size or location of the region of interest. Accordingly, for the data structure generated in operation 510, a structure having high data retrieval efficiency is more appropriate than a structure having high data insertion or removal efficiency.

For example, the data structure may be a tree efficient for searching for cells within a pathological slide image, and may be implemented as, for example, a K-D tree, a ball tree, or the like, but is not limited thereto. The tree generated by the processor 110 may be used even when visualizing locations of cells within an image area output to the display apparatus.

Meanwhile, in the same method as in operation 510, the processor 110 may generate a data structure even for grids set in the pathological slide image by using coordinate values of the grids.

In operation 520, the processor 110 identifies, from the data structure, coordinate information corresponding to at least one cell included in a region of interest.

The processor 110 identifies a location and a size of the region of interest, and searches for, via the data structure, coordinate values of cells included within the region of interest. For example, when the data structure is a certain tree, the processor 110 searches for coordinate values of cells within the tree.

In operation 530, the processor 110 generates quantitative information on the basis of the number corresponding to the identified coordinate information.

The processor 110 generates the quantitative information by counting the number of coordinate values searched for in operation 520. For example, the quantitative information may include the number of total cells included in the region of interest, the number of particular cells included in the region of interest, or the like.

Figure 6:
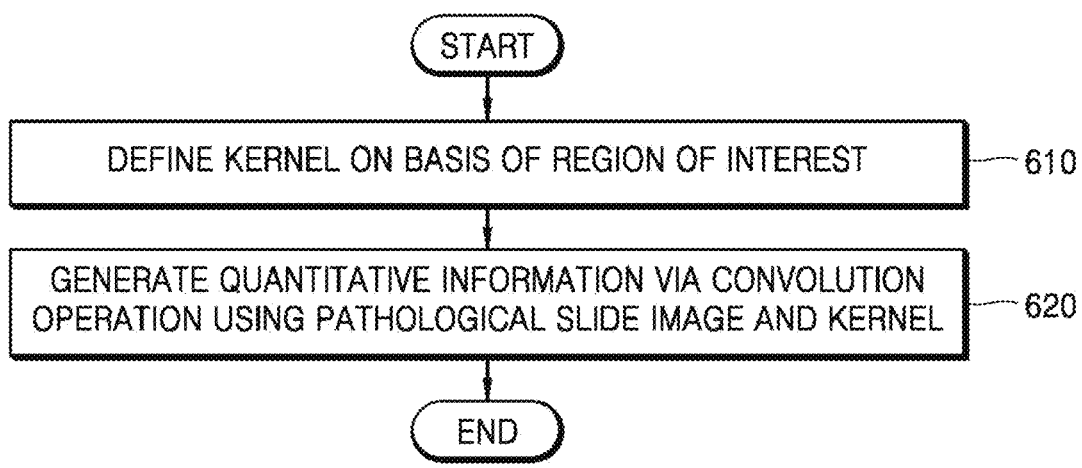
FIG. 6 is a flowchart illustrating another example in which a processor generates quantitative information, according to an embodiment.

FIG. 6 is a flowchart illustrating another example in which a processor generates quantitative information, according to an embodiment.

The processor 110 may generate quantitative information by calculating the number of or particular statistical values for cells in a region of interest. A corresponding region of interest is set in any one pixel in a pathological slide image, and thus, when the user 30 designates a particular pixel via an input device (e.g., a mouse, or the like), the processor 110 may read the number of or particular statistical values for cells in the region of interest corresponding to the pixel. An example in which the processor 110 calculates the number of or particular statistical values for cells in a region of interest will be described with reference to FIG. 6.

In operation 610, the processor 110 defines a kernel on the basis of a region of interest.

Here, at least one kernel is defined according to a type of quantitative information. As described above with reference to FIG. 4, a size or shape of the region of interest may be defined by the user 30. The processor 110 determines, on the basis of an input of the user 30, a type of quantitative information to be acquired from the region of interest. For example, the type of quantitative information may correspond to the number of total cells (or particular types of cells), the density of total cells (or particular types of cells), a ratio between different cells, a proportion of particular types of cells to the total cells, or the like. The processor 110 defines a kernel according to the size and shape of the region of interest, and the type of quantitative information. Hereinafter, an example in which the processor 110 defines a kernel will be described with reference to FIG. 7.

Figure 7:
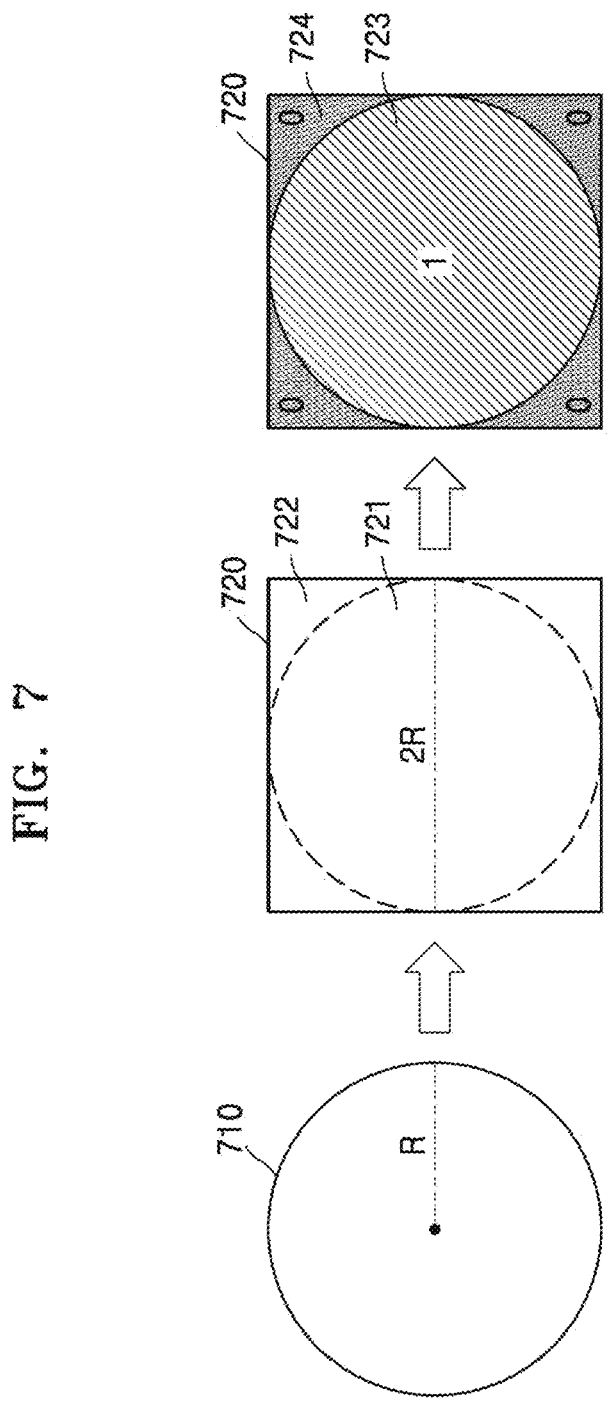
FIG. 7 is a view illustrating an example in which a processor defines a kernel, according to an embodiment.

FIG. 7 is a view illustrating an example in which a processor defines a kernel, according to an embodiment.

As a first example, a type of quantitative information may be the number of cancer cells. Also, at a particular magnification of a pathological slide image, a region of interest 710 may be a circle having a radius R. In addition, a channel may be an image in which "1" is written in a pixel corresponding to a cancer cell, and "0" is written in remaining pixels. For example, "1" may be written in a pixel corresponding to the center of a cancer cell.

The processor 110 sets a kernel 720 including the whole region of interest 710. For example, the processor 110 may set a square having a side length of 2R as the kernel 720. Accordingly, the kernel 720 may be divided into a region 721 included in the region of interest 710 and a region 722 that is not included in the region of interest 710. The processor 110 may define the kernel 720 by writing "1" in the region 721 and writing "0" in the region 722.

As a second example, the type of quantitative information may be a ratio of the number of cancer cells to the number of all types of cells. Also, at a particular magnification of a pathological slide image, the region of interest 710 may be a circle having a radius R. In addition, a first channel may be an image in which "1" is written in a pixel corresponding to the center of a cancer cell and "0" is written in remaining pixels. Also, a second channel may be an image in which "1" is written in a pixel corresponding to the center of all cells and "0" is written in remaining pixels.

The processor 110 sets a first kernel and a second kernel including a whole region of interest. For example, the processor 110 may set the first kernel and the second kernel by a square having a side length of 2R. Accordingly, the first kernel and the second kernel may be divided into a region included in the region of interest and a region that is not included in the region of interest. The processor 110 may define the first kernel and the second kernel by writing "1" in the region included in the region of interest and writing "0" in the region that is not included in the region of interest.

Referring to FIG. 6 again, in operation 620, the processor 110 generates quantitative information via a convolution operation using a pathological slide image and the kernel. Hereinafter, an example in which the processor 110 performs a convolution operation will be described with reference to FIG. 8.

Figure 8:
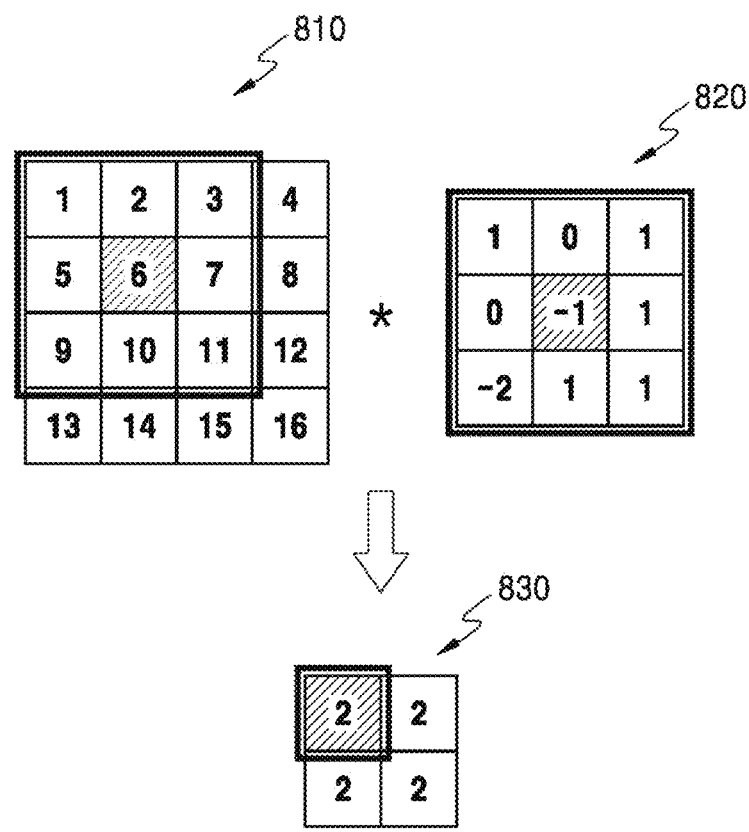
FIG. 8 is a view illustrating an example of a convolution operation according to an embodiment.

FIG. 8 is a view illustrating an example of a convolution operation according to an embodiment.

FIG. 8 shows a channel 810 and a kernel 820 used for a convolution operation. Also, FIG. 8 shows a result 830 of the convolution operation performed by the channel 810 and the kernel 820. FIG. 8 illustrates that a size of the channel 810 is 4*4 and a size of the kernel 820 is 2*2, but the present disclosure is not limited thereto.

The processor 110 overlaps the channel 810 and the kernel 820 to perform a sum of product operation, and after the operation, moves the kernel by one space in a particular direction to perform the sum of product operation again. In the same method as described above, the processor 110 derives the result 830 by performing a convolution operation by using the channel 810 and the kernel 820.

In the first example of FIG. 7, the processor 110 may calculate the number of cancer cells in a region of interest corresponding to each of all pixels included in a channel by performing a convolution operation on the channel and a kernel. Accordingly, the processor 110 may generate the number of cancer cells within the region of interest as quantitative information.

In the second example of FIG. 7, the processor 110 may calculate the number of cancer cells within a region of interest by performing a convolution operation on a first channel and a first kernel. Also, the processor 110 may calculate the number of total cells in the region of interest by performing a convolution operation on a second channel and a second kernel. Accordingly, the processor 110 may generate, as quantitative information, a ratio of the number of cancer cells to the number of all types of cells in the region of interest.

Referring to FIG. 4 again, in operation 420, the processor 110 generates qualitative information regarding at least one tissue included in the pathological slide image by analyzing the pathological slide image.

The method for the processor 110 to analyze the pathological slide image is the same as described above with reference to operation 410. Meanwhile, the qualitative information may include information regarding whether or not programmed death-ligand 1 (PD-L1) is expressed in a cell included in the corresponding tissue. For example, the qualitative information may include information regarding whether a corresponding cell is a PD-L1 positive tumor cell, a PD-L1 negative tumor cell, a PD-L1 positive lymphocyte, or a PD-L1 positive macrophage. For example, which type of above-described cells a corresponding cell belongs to may be expressed in a certain color, and thus, qualitative information may be output in a certain color to the display apparatus. Hereinafter, examples in which a processor generates qualitative information will be described with reference to FIGS. 9 and 10.

Figure 9:
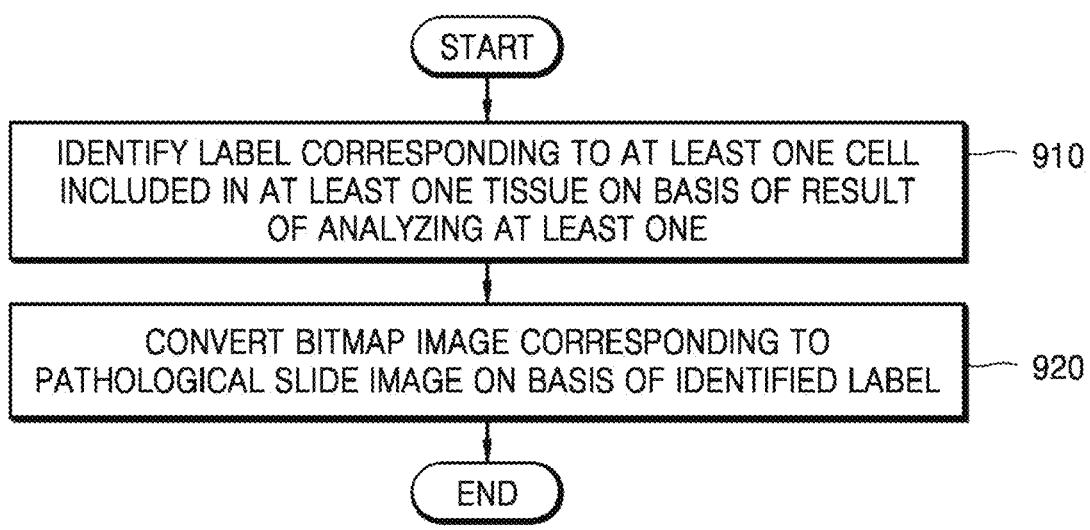
FIG. 9 is a flowchart illustrating an example in which a processor generates qualitative information, according to an embodiment.

FIG. 9 is a flowchart illustrating an example in which a processor generates qualitative information, according to an embodiment.

A result of analyzing a tissue (e.g., a tissue segmentation result, such as s PD-L1 tumor proportion score (TPS), s PD-L1 combined positive score (CPS), a cancer area, or cancer stroma) is generated as a bitmap image having a lower resolution than a resolution of an original of a pathological slide image, and each pixel of the bitmap image has, as a pixel value, a label ID of a tissue present at a corresponding location. Here, the label ID may be expressed by a number. The processor 110 may generate qualitative information by using label information according to the following process.

In operation 910, the processor 110 identifies, on the basis of an analysis result of at least one tissue, label information corresponding to at least one cell included in the at least one tissue.

First, the processor 110 identifies label information regarding each of cells, or tissues in the body. Here, the label information includes an ID, a color, and a title of each label. Also, the processor 110 determines a type of cell or tissue by analyzing a pathological slide image. In addition, the processor 110 searches for, from among the identified label information, label information corresponding to at least one cell or tissue included in the pathological slide image.

In operation 920, the processor 110 converts a bitmap image corresponding to the pathological slide image on the basis of the identified label information.

The processor 110 sets, as a color value of a label color, a pixel value corresponding to each cell within the bitmap image by using a color (i.e., a label color) within the label information retrieved in operation 910. Accordingly, a pixel of each cell expressed in the bitmap image may be set to a label color suitable for a feature of a tissue.

Meanwhile, even when a resolution of the bitmap image is lower than a resolution of the pathological slide image, a size of the bitmap image is large due to a large size of the pathological slide image, and thus, the processor 110 may not be able to fully load the bitmap image. In this case, the processor 110 may convert the bitmap image in a different method on the basis of a resource of an apparatus (e.g., the user terminal 100) for converting a bitmap image. For example, the processor 110 segments the bitmap image into a plurality of tiles on the basis of the resource of the apparatus for converting a bitmap image. Also, the processor 110 converts each of the tiles on the basis of the identified label information. In addition, the processor 110 combines the converted tiles.

For example, the processor 110 may use a WebGL capable of utilizing a GPU embedded in the apparatus to convert the bitmap image to a label color (operation 920). In detail, the processor 110 loads the bitmap image into the WebGL as 2D texture, samples the corresponding texture in a fragment shader, and renders the sampled texture by using a color value corresponding to the sampled label ID. However, even when the resolution of the bitmap image is lower than the resolution of the original pathological slide image, the bitmap image may not be fully loaded as 2D texture into the GPU when a size of the original pathological slide image is significantly large. In this case, the processor 110 may divide the bitmap image into a plurality of tiles, and may perform a task of converting the bitmap image on the basis of the tiles. An example in which the processor 110 performs a task of converting a bitmap image on the basis of tiles will be described with reference to FIG. 10.

Figure 10:
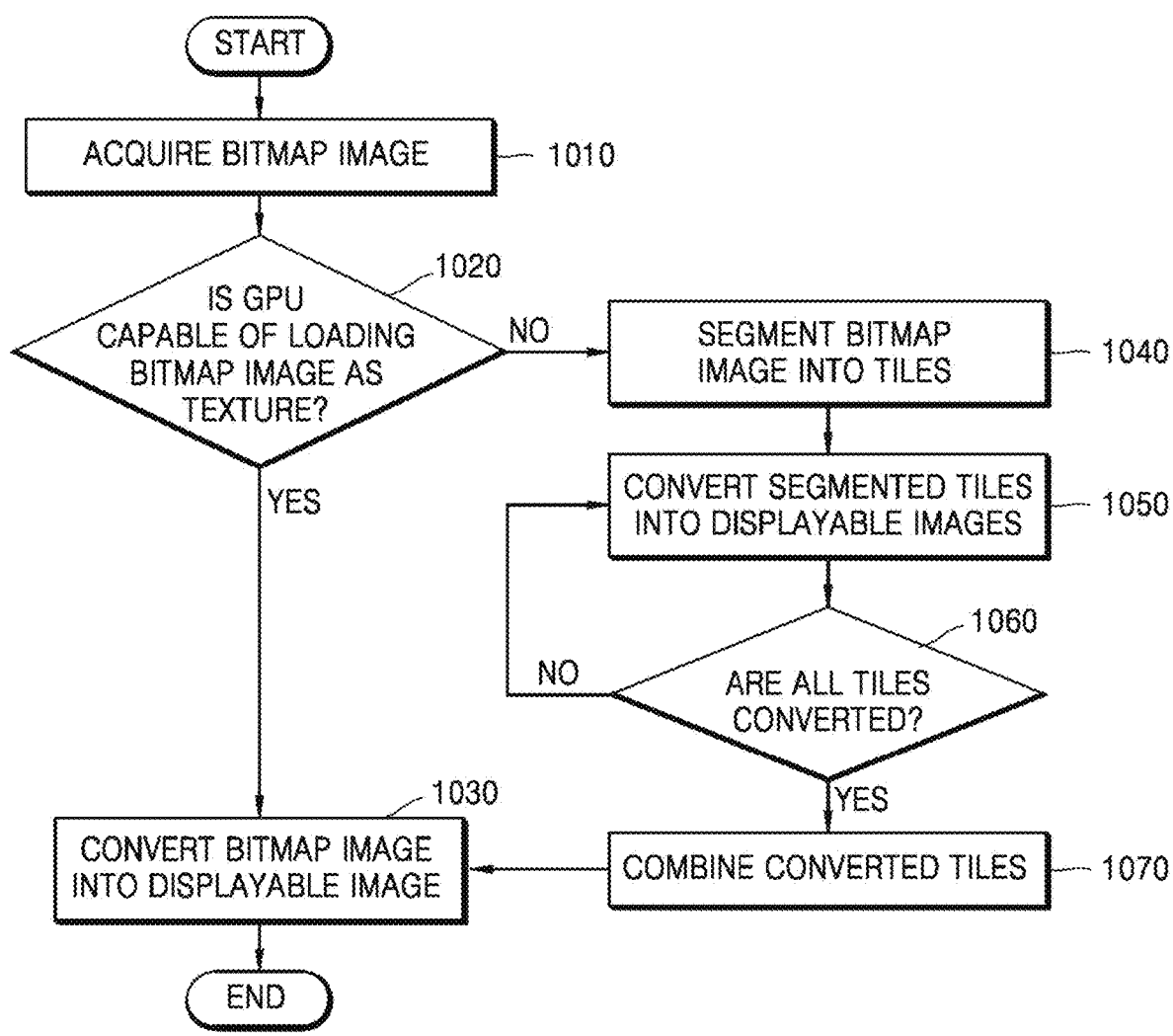
FIG. 10 is a flowchart illustrating another example in which a processor generates qualitative information, according to an embodiment.

FIG. 10 is a flowchart illustrating another example in which a processor generates qualitative information, according to an embodiment.

In operation 1010, the processor 110 acquires a bitmap image.

In operation 1020, the processor 110 determines whether or not a GPU may load the bitmap image as texture. Here, the texture may be a 2D texture.

When the GPU is capable of loading the bitmap image as the texture, operation 1030 is performed, and otherwise, operation 1040 is performed.

In operation 1030, the processor 110 converts the bitmap image into a displayable image. For example, the processor 110 converts the bitmap image according to the method described above with reference to operation 920. Also, the processor 110 converts the converted bitmap image into an image that may be output to the display apparatus.

In operation 1040, the processor 110 segments the bitmap image into tiles. For example, the processor 110 may segment the bitmap image into ¼ of a maximum size of an image that may be loaded as texture into the GPU, but is not limited thereto.

In operation 1050, the processor 110 converts the segmented tiles into displayable images. For example, the processor 110 converts each of the tiles according to the method described above with reference to operation 920.

Also, the processor 110 converts the converted tiles into images that may be output to the display apparatus.

In operation 1060, the processor 110 determines whether or not conversion tasks for all the tiles are completed. When the conversion tasks for all the tiles are completed, operation 1070 is performed, and otherwise, operation 1050 is additionally performed.

In operation 1070, the processor 110 combines the converted tiles. In detail, the processor 110 generates a product corresponding to the whole bitmap image by connecting the converted tiles to one another.

Referring to FIG. 4 again, in operation 430, the processor 110 outputs at least one of the quantitative information and the qualitative information on the pathological slide image according to a manipulation of the user 30.

For example, the processor 110 may output qualitative information corresponding to at least a portion of the pathological slide image and quantitative information corresponding to the region of interest. A portion or the entire portion of the pathological slide image may be output to the display apparatus. Also, a region of interest may be set in a portion of an image output to the display apparatus. In this case, the processor 110 may output qualitative information regarding the whole image output to the display apparatus (e.g., output a color corresponding to a tissue), and may output quantitative information regarding a region of interest (e.g., output the number of particular types of cells included in the region of interest, a TPS, a CPS, or TIL density).

Meanwhile, the processor 110 may adaptively output quantitative information and/or qualitative information in response to a change in image output on the display apparatus according to a manipulation of the user 30.

As an example, the processor 110 may change and output at least one of quantitative information and qualitative information on the basis of an output portion or an output magnification of the pathological slide image changed according to the manipulation of the user 30. For example, whenever the user 30 enlarges or reduces the pathological slide image, an analysis result (quantitative information and/or qualitative information) suitable for the area may be provided, and an analysis result of an area other than the area output to the display apparatus may not be provided.

As another example, the processor 110 may change and output at least one of quantitative information and qualitative information by comparing an output magnification of the pathological slide image changed according to a user's manipulation with a threshold magnification. For example, a particular analysis result may be provided only when the user 30 enlarges the pathological slide image to a certain magnification or higher. Alternatively, an analysis result, which is provided before the user 30 enlarges the pathological slide image, may not be provided when enlarging the pathological slide image to a certain magnification or higher.

Figure 11:
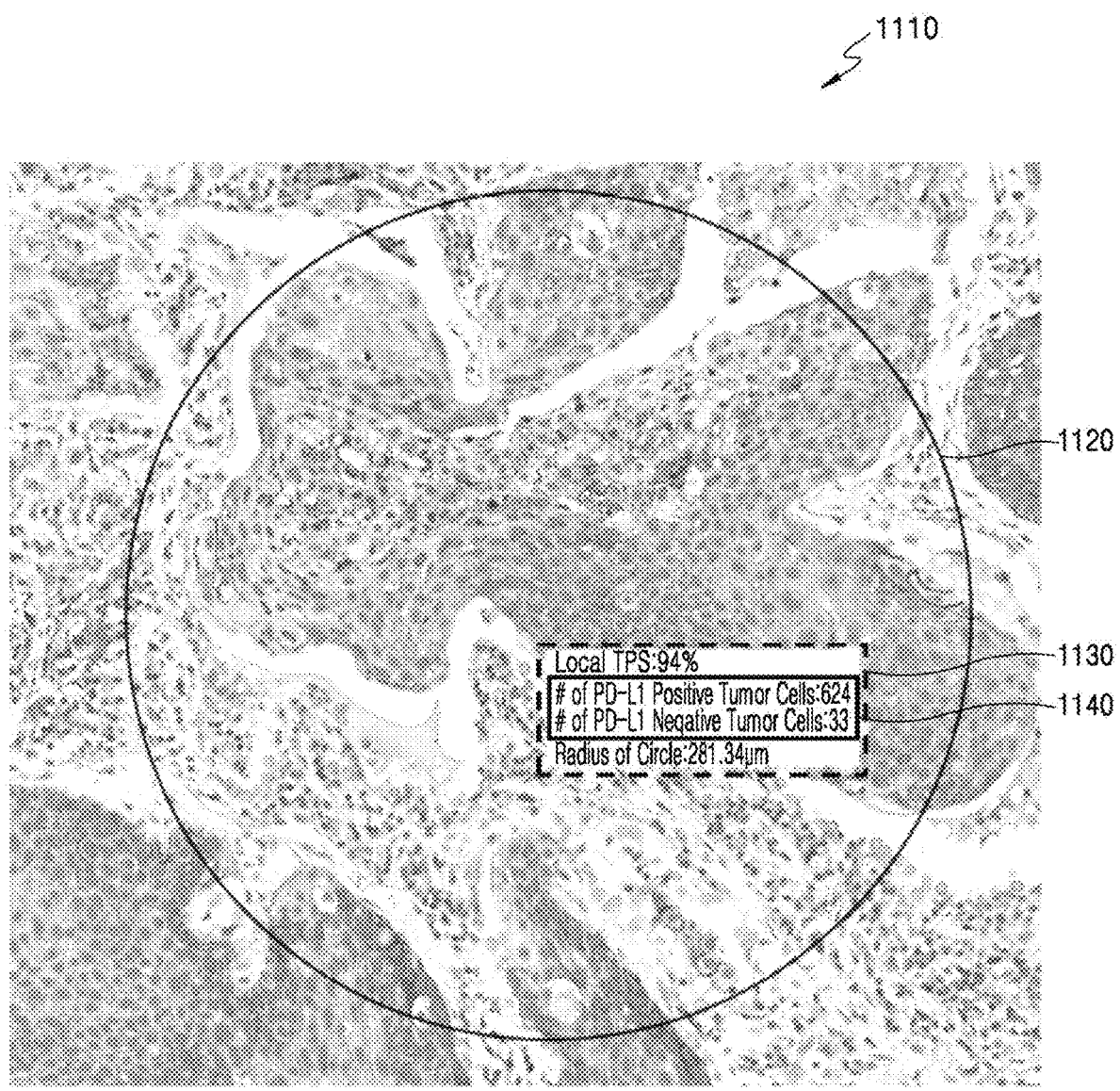
FIGS. 11 and 12 are views illustrating examples in which quantitative information is output, according to an embodiment.
Figure 12:
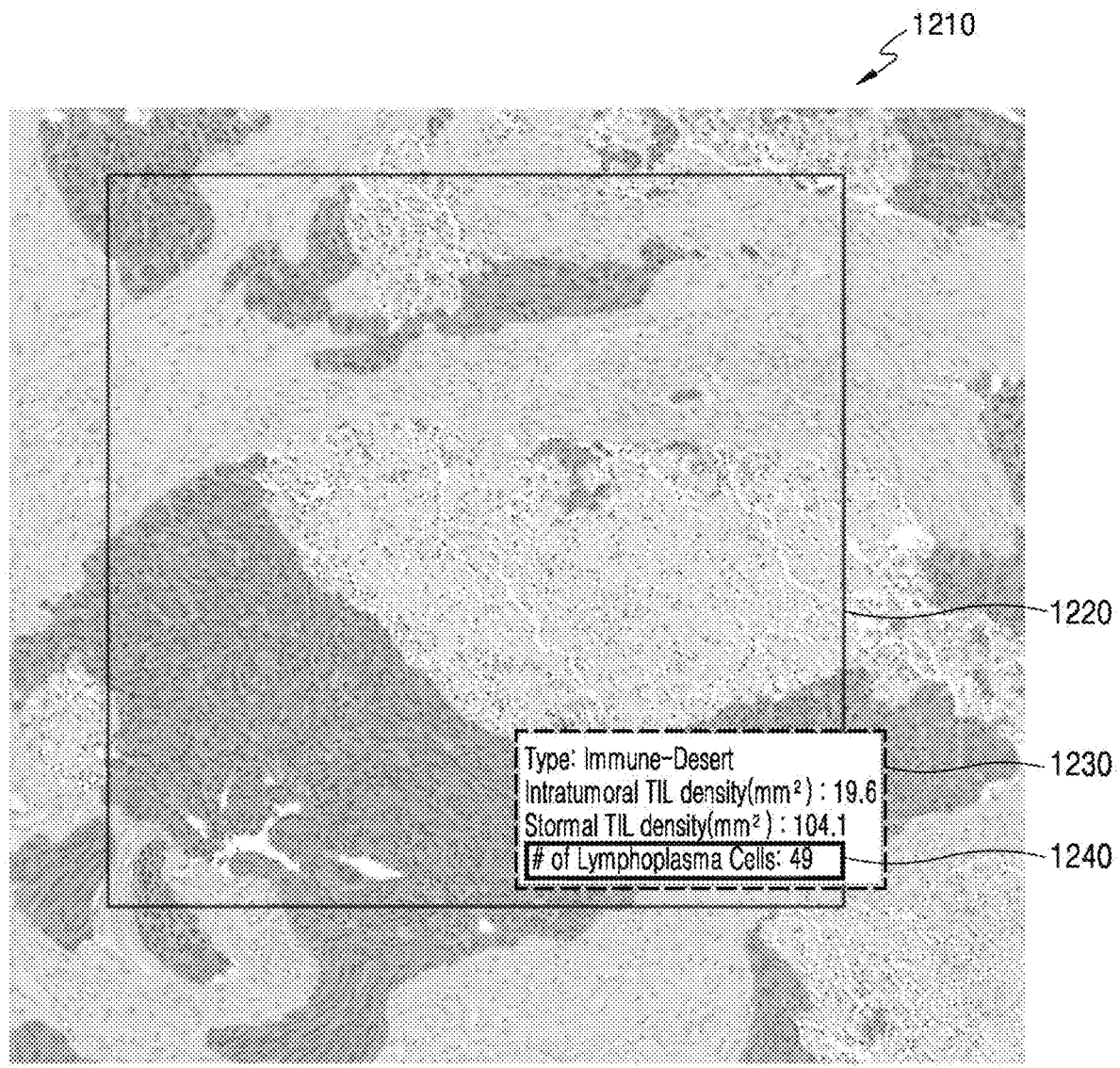

FIGS. 11 and 12 are views illustrating examples in which quantitative information is output, according to an embodiment.

FIGS. 11 and 12 illustrate portions 1110 and 1210 of a pathological slide image output to a display apparatus. Regions of interest 1120 and 1220 may be set on the pathological slide image according to a manipulation of the user 30. Also, sizes and locations of the regions of interest 1120 and 1220 may be changed according to a manipulation of the user 30.

When the regions of interest 1120 and 1220 are set, the processor 110 generates and outputs quantitative information 1130 and 1230 of cells included in the regions of interest 1120 and 1220. The quantitative information 1130 and 1230 may include the numbers 1140 and 1240 of particular types of cells included in the regions of interest 1120 and 1220, but are not limited thereto.

Figure 14:
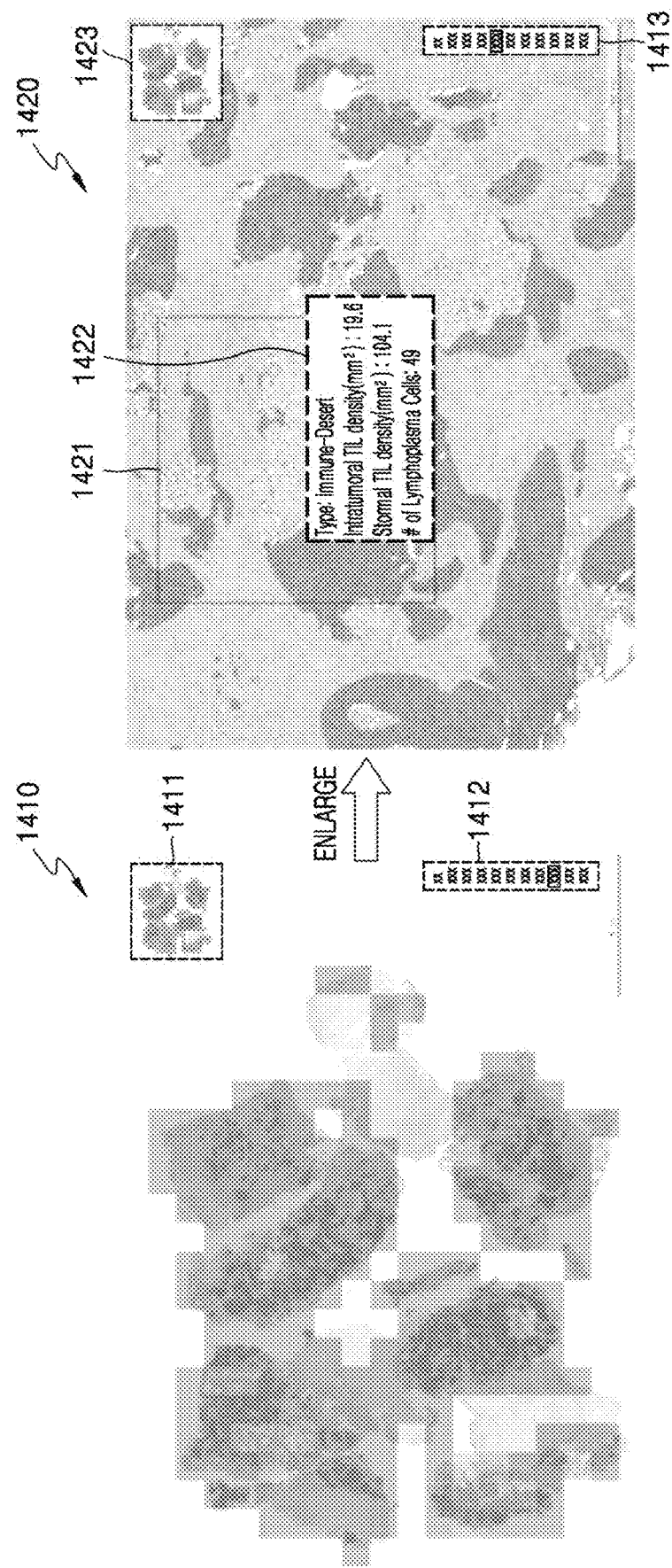

FIGS. 13 and 14 are views illustrating examples in which quantitative information and qualitative information are output, according to an embodiment.

Referring to FIG. 13, locations of cancer cells may not be output in an image 1310 (i.e., a whole pathological slide image) before enlarged, and the number of cancer cells may also not be output. Only qualitative information (e.g., information representing a feature of a tissue in a color) may be output in the image 1310 before enlarged. For example, the feature of the tissue may indicate whether a ratio of PD-L1 positive cancer cells to PD-L1 negative cancer cells within a certain size circle region centered on each pixel is greater than or equal to a certain threshold value. When the user 30 enlarges the image 1310 to a threshold magnification or higher, a location of a cancer cell may be output on an enlarged image 1320. For example, a location of a cell may be indicated as dots having different colors according to whether a type of each cell is a PD-L1 positive tumor cell or a PD-L1 negative tumor cell. Also, a region of interest 1321 may be set in the image 1320, and quantitative information 1322 regarding the region of interest 1321 may be output. At least one of a TPS for the region of interest 1321, the number of total cells within the region of interest 1321, an area of the region of interest 1321, the number of PD-L1 positive tumor cells within the region of interest 1321, and the number of PD-L1 negative tumor cells within the region of interest 1321 may be output as the quantitative information 1322 regarding the region of interest 1321.

Meanwhile, on one side of a screen, thumbnail images 1311 and 1323 representing images 1310 and 1320 may be output, and images 1312 and 1324 representing current magnifications of the images 1310 and 1320 may also be output.

Also, on one side of the screen, a control panel (not shown) may be output, and locations of cancer cells may be displayed or removed by selecting and/or deselecting a check box within the control panel (not shown). In addition, a PD-L1 TPS map may be displayed or removed by selecting and/or deselecting the check box within the control panel (not shown).

Meanwhile, referring to FIG. 14, according to a user's manipulation (e.g., enlargement of a pathological slide image or the like), previously output first qualitative information may be changed to another second qualitative information and output. In addition, certain quantitative information, which is not output before the user's manipulation is received, may be additionally output.

For example, the first qualitative information may be an immune phenotype (IP) corresponding to at least a portion 1410 of a pathological slide image that is output before a manipulation of the user is received, and the second qualitative information may a feature of at least one of a tissue and a cell included in the at least portion 1420 of the pathological slide image that is output according to a manipulation the user. However, the first qualitative information and the second qualitative information are not limited to the above description. In addition, the certain quantitative information may be a density of immune cells included in the at least portion 1420 of the pathological slide image that is output according to a manipulation of the user, but is not limited thereto.

For example, only qualitative information (e.g., information representing a feature of a tissue in a color) may be output in an image 1410 before enlarged. For example, the feature of the tissue may indicate an IP. The IP may be determined on the basis of quantitative information. For example, the IP may be determined on the basis of at least one of the number, distribution, and density of immune cells within at least a partial region of a pathological slide.

The IP may be displayed in various classification methods. As an example, an IP for each grid may be determined on the basis of at least one of a density of immune cells in a cancer area and a density of immune cells in a cancer stroma on the grid. For example, the IP may be indicated by at least one of immune inflamed, immune excluded, and immune desert according to what range a value calculated on the basis of at least one of the density of immune cells in the cancer area and the density of immune cells in the cancer stroma falls within.

A map for cells and tissues may not be output in the image 1410 before enlarged to better identify an IP map.

When the user 30 enlarges the image 1410 to a threshold magnification or higher, a map for features of cells and tissues may be output instead of the IP map. In other words, the processor 110 may output a location of at least one cell (e.g., a lymphoplasma cell) on the screen. The processor 110 may output information regarding each region on the screen instead of the IP map. For example, the processor 110 may identify each region on the screen as one of a cancer area, a cancer stroma area, a necrosis area, and a background area, and may overlay a corresponding color thereon.

Also, a region of interest 1421 may be set in the image 1420, and quantitative information 1422 regarding the region of interest 1421 may be output. At least one of a density of immune cells within a cancer area included in the region of interest 1421, a density of immune cells within a cancer stroma included in the region of interest 1421, and the number of immune cells within the region of interest 1421 may be output as the quantitative information 1422 regarding the region of interest 1421.

Meanwhile, on one side of the screen, thumbnail images 1411 and 1423 representing the images 1410 and 1420 may be output, and images 1412 and 1413 representing current magnifications of the images 1410 and 1420 may also be output.

In addition, on one side of the screen, a control panel (not shown) may be output, and at least one location may be displayed or removed by selecting and/or deselecting a check box within the control panel (not shown). Also, an IP map and/or a histological feature map may be displayed or removed by selecting and/or deselecting the check box within the control panel (not shown).

Figure 15:
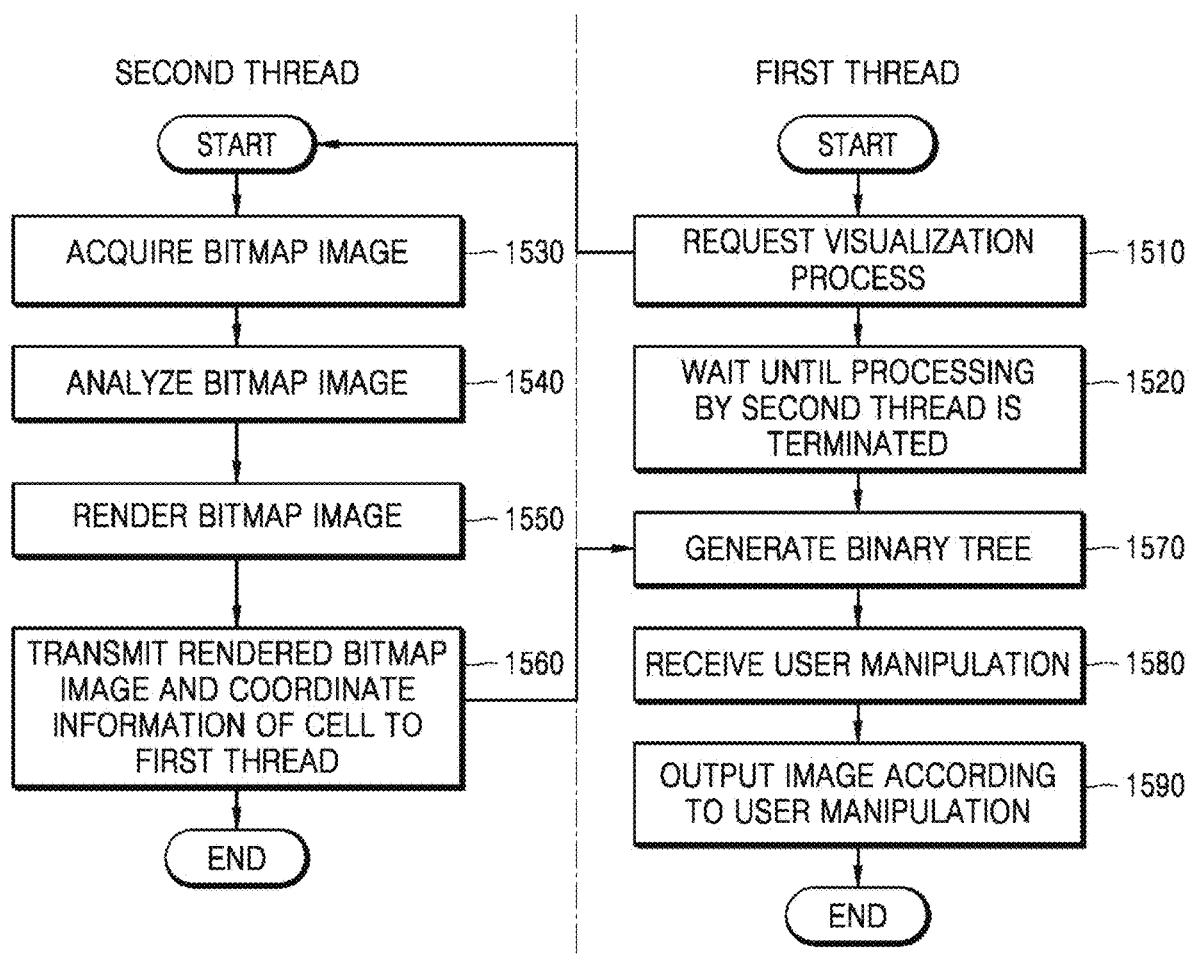
FIG. 15 is a flowchart illustrating an example in which a processor outputs information regarding a pathological slide image, according to an embodiment.

FIG. 15 is a flowchart illustrating an example in which a processor outputs information regarding a pathological slide image, according to an embodiment.

The processor 110 may process the above-described processes via a plurality of threads to generate and output quantitative information and/or qualitative information by analyzing a pathological slide image. Accordingly, the processor 110 may reduce a time taken for processing the processes, and thus may output related information to the display apparatus in real time according to a manipulation of the user 30.

For example, referring to FIG. 15, a first thread may receive a manipulation of the user 30, and may request a task corresponding to the manipulation of the user 30 from a second thread. In addition, the second thread may transmit a result of processing the requested task to the first thread, and the first thread may output an image and related information to the display apparatus by using the received result.

In operation 1510, a request for a visualization process is received via the first thread. Here, the request for the visualization process includes enlarging or reducing a pathological slide image, changing a location of a region of interest, or increasing or reducing a size of the region of interest according to a manipulation of the user 30.

In operation 1520, the first thread waits until the processing by the second thread is terminated.

In operations 1530 to 1550, the second thread performs tasks of acquiring, analyzing, and rendering a bitmap image. Operations 1530 to 1550 correspond to the operations of the processor 110 described above with reference to FIGS. 4 to 10. Accordingly, a detailed description of operations 1530 to 1550 will be omitted herein.

In operation 1560, the second thread transmits the rendered bitmap image and coordinate information of a cell to the first thread. Then, in operation 1570, the first thread generates a binary tree by using information transmitted from the second thread.

In operations 1580 and 1590, the first thread receives a manipulation of the user 30, and outputs an image on the display apparatus in response to the manipulation of the user 30. Here, the image represents an image in which at least one of quantitative information and qualitative information as well as at least a portion of the pathological slide image is displayed.

As described above, the processor 110 outputs quantitative information or qualitative information in correspondence to a region of interest set according to a manipulation of the user 30 or at least a portion of a pathological slide image output on the display apparatus. Accordingly, the user 30 may be given effective help to read an image output on the display apparatus and diagnose a subject.

Meanwhile, the above-described method may be written as a program that may be executed on a computer, and may be implemented in a general-purpose digital computer that operates the program by using a computer-readable recording medium. In addition, a structure of data used in the above-described method may be recorded in a computer-readable recording medium via various types of means. The computer-readable recording medium includes a storage medium, such as a magnetic storage medium (e.g., ROM, RAM, a USB, a floppy disk, a hard disk, or the like) and an optically readable medium (e.g., CD-ROM, DVD, or the like).

One of ordinary skill in the art related to the present embodiment will understand that the present embodiment may be implemented in a modified form within the scope that does not depart from the essential characteristics of the above description. Therefore, the disclosed methods should be considered in an illustrative rather than a restrictive sense, and the scope of the present disclosure should be defined by claims rather than the foregoing description, and should be construed to include all differences within the scope equivalent thereto.

The invention claimed is:

1. A system for outputting information regarding a pathological slide image comprising:
   at least one memory; and
   at least one processor, wherein
   the processor generates quantitative information regarding at least one cell included in a pathological slide image by analyzing the pathological slide image, generates qualitative information regarding at least one tissue included in the pathological slide image by analyzing the pathological slide image, and controls a display apparatus to output at least one of the quantitative information and the qualitative information on the pathological slide image according to a manipulation of a user, wherein the processor controls the display apparatus to change and output at least one of the quantitative information and the qualitative information based on an output portion or an output magnification of the pathological slide image changed according to the manipulation of the user.

2. The system of claim 1, wherein the processor generates a data structure by using coordinate information corresponding to each of cells included in the pathological slide image, identifies, from the data structure, coordinate information corresponding to at least one cell included in a region of interest, and generates the quantitative information based on a number corresponding to the identified coordinate information.

3. The system of claim 1, wherein the processor defines a kernel based on a region of interest, and generates the quantitative information via a convolution operation using the pathological slide image and the kernel.

4. The system of claim 1, wherein the processor identifies label information corresponding to at least one cell included in the at least one tissue based on a result of analyzing the at least one tissue, and converts a bitmap image corresponding to the pathological slide image based on the identified label information.

5. The system of claim 1, wherein the processor controls the display apparatus to output qualitative information corresponding to at least a portion of the pathological slide image and quantitative information corresponding to a region of interest.

6. The system of claim 1, wherein the processor controls the display apparatus to change and output at least one of the quantitative information and the qualitative information by comparing an output magnification of the pathological slide image changed according to the manipulation of the user with a threshold magnification.

7. A method of outputting information regarding a pathological slide image, the method comprising:
generating quantitative information regarding at least one cell included in the pathological slide image by analyzing the pathological slide image;
generating qualitative information regarding at least one tissue included in the pathological slide image by analyzing the pathological slide image; and
outputting at least one of the quantitative information and the qualitative information on the pathological slide image according to a manipulation of a user,
wherein the outputting includes changing and outputting at least one of the quantitative information and the qualitative information based on an output portion or an output magnification of the pathological slide image changed according to the manipulation of the user.

8. The method of claim 7, wherein the generating the quantitative information includes:
generating a data structure by using coordinate information corresponding to each of cells included in the pathological slide image;
identifying, from the data structure, coordinate information corresponding to at least one cell included in a region of interest; and
generating the quantitative information based on a number corresponding to the identified coordinate information.

9. The method of claim 7, wherein the generating the quantitative information includes:
defining a kernel based on a region of interest; and
generating the quantitative information via a convolution operation using the pathological slide image and the kernel.

10. The method of claim 7, wherein the generating the qualitative information includes:
identifying label information corresponding to at least one cell included in the at least one tissue based on a result of analyzing the at least one tissue; and
converting a bitmap image corresponding to the pathological slide image based on the identified label information.

11. The method of claim 7, wherein the outputting includes outputting qualitative information corresponding to at least a portion of the pathological slide image and quantitative information corresponding to a region of interest.

12. The method of claim 7, wherein the outputting includes performing, based on a manipulation of the user, a change of previously output first qualitative information to second qualitative information and an output of certain quantitative information, the first qualitative information includes an immune phenotype (IP) corresponding to at least a portion of the pathological slide image output before the manipulation of the user is received, the second qualitative information includes a feature of at least one of a tissue and a cell included in at least a portion of the pathological slide image output according to the manipulation of the user, and the certain quantitative information includes a density of immune cells included in at least a portion of the pathological slide image output according to the manipulation of the user.

13. A non-transitory computer-readable recording medium recording thereon a program for executing the method of claim 7 on a computer.

* * * * *